(12) United States Patent
Rotter et al.

(10) Patent No.: US 9,857,292 B2
(45) Date of Patent: *Jan. 2, 2018

(54) BROADBAND AND WIDE FIELD ANGLE COMPENSATOR

(71) Applicant: KLA-Tencor Corporation, Milpitas, CA (US)

(72) Inventors: Lawrence Rotter, Pleasanton, CA (US); Klaus Flock, Sunnyvale, CA (US); Muzammil Arain, Milpitas, CA (US); David Y. Wang, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/344,704

(22) Filed: Nov. 7, 2016

(65) Prior Publication Data

US 2017/0052112 A1     Feb. 23, 2017

Related U.S. Application Data

(63) Continuation of application No. 14/466,369, filed on Aug. 22, 2014, now Pat. No. 9,519,093.

(Continued)

(51) Int. Cl.
*G01J 4/00*     (2006.01)
*G01N 21/23*    (2006.01)
(Continued)

(52) U.S. Cl.
CPC ........... *G01N 21/23* (2013.01); *G01N 21/211* (2013.01); *G01N 21/9501* (2013.01);
(Continued)

(58) Field of Classification Search
CPC ............... G02B 5/3083; G01N 21/211; G01N 2021/213; G02F 1/13363
See application file for complete search history.

(56) References Cited

U.S. PATENT DOCUMENTS 3,904,267 A    9/1975    de Veer
6,181,421 B1   1/2001    Aspnes et al.
(Continued)

FOREIGN PATENT DOCUMENTS

EP    1436656 A2    6/2004
EP    1483616 A1    12/2004
(Continued)

OTHER PUBLICATIONS

International Search Report and Written Opinion dated Dec. 2, 2014, for PCT Application No. PCT/US2014/052373 filed on Aug. 22, 2014, by KLA-Tencor Corporation, 14 pages.
(Continued)

*Primary Examiner* — Michael A Lyons
*Assistant Examiner* — Maurice Smith
(74) *Attorney, Agent, or Firm* — Spano Law Group; Joseph S. Spano

(57) ABSTRACT

A rotatable compensator configured to transmit non-collimated light over a broad range of wavelengths, including ultraviolet, with a high degree of retardation uniformity across the aperture is presented. In one embodiment, a rotatable compensator includes a stack of four individual plates in optical contact. The two thin plates in the middle of the stack are made from a birefringent material and are arranged to form a compound, zeroth order bi-plate. The remaining two plates are relatively thick and are made from an optically isotropic material. These plates are disposed on either end of the compound, zeroth order bi-plate. The low order plates minimize the sensitivity of retardation across (Continued)

the aperture to non-collimated light. Materials are selected to ensure transmission of ultraviolet light. The optically isotropic end plates minimize coherence effects induced at the optical interfaces of the thin plates.

20 Claims, 4 Drawing Sheets

Related U.S. Application Data

(60) Provisional application No. 61/869,065, filed on Aug. 23, 2013.

(51) Int. Cl.
  *G02B 5/30* (2006.01)
  *G01N 21/21* (2006.01)
  *G02F 1/13363* (2006.01)
  *G01N 21/95* (2006.01)

(52) U.S. Cl.
  CPC ......... *G02B 5/3083* (2013.01); *G02B 5/3091* (2013.01); *G02F 1/13363* (2013.01); *G01N 2021/213* (2013.01); *G01N 2201/068* (2013.01)

(56) References Cited

U.S. PATENT DOCUMENTS

| 6,278,519 | B1 | 8/2001 | Rosencwaig et al. |
|---|---|---|---|
| 6,631,001 | B2 | 10/2003 | Kulseko |
| 7,193,710 | B1 | 3/2007 | Johs et al. |
| 7,548,370 | B2 | 6/2009 | Albert et al. |
| 7,889,339 | B1 | 2/2011 | Flock et al. |
| 7,916,391 | B2 | 3/2011 | Albert et al. |
| 7,969,543 | B2 | 6/2011 | Kwok et al. |
| 8,031,326 | B2 | 10/2011 | Totzeck et al. |
| 8,049,866 | B2 | 11/2011 | McCarthy |
| 8,120,848 | B2 | 2/2012 | Isano |
| 8,502,979 | B2 | 8/2013 | Levy et al. |
| 2004/0001255 | A1 | 1/2004 | Fratello |
| 2005/0195480 | A1* | 9/2005 | Brown ................. G02B 5/3083 359/489.07 |
| 2007/0091311 | A1 | 4/2007 | Aspnes |
| 2008/0174759 | A1 | 7/2008 | Schuster |
| 2013/0271741 | A1 | 10/2013 | Saenger |

FOREIGN PATENT DOCUMENTS

| JP | 2000-065531 | 1/2011 |
|---|---|---|
| WO | 0190687 A2 | 11/2001 |
| WO | 03029856 A2 | 4/2003 |
| WO | 03077011 A1 | 9/2003 |

OTHER PUBLICATIONS

Holmes, D.A., "Exact Theory of Retardation Plates," J. Opt. Soc. Am., 54 (1964) 1115-1120.

Hale, P.D. and Day, G.W., Stability of birefringent linear retarders (waveplates), Appl. Opt. 27 (1988) 5146-5153.

Pancharatnam, S., "Achromatic combinations of birefringent plates. Part I. An achromatic circular polarizer," Proc. Indian Acad. Sci. A41, 130-136.

Pancharatnam, S., "Achromatic combinations of birefringent plates. Part II. An achromatic quarter-wave plate," Proc. Indian Acad. Sci. A41, 137-144.

Yeh, P. and Gu, C., "Optics of Liquid Crystal Displays," Ch. 4.7-4.10, Wiley, Hoboken, New Jersey, 2010.

\* cited by examiner

BROADBAND AND WIDE FIELD ANGLE COMPENSATOR

CROSS REFERENCE TO RELATED APPLICATION

The present application for patent is a continuation of, and claims priority under 35 U.S.C. §120 from, U.S. patent application Ser. No. 14/466,369, entitled "Broadband And Wide Field Angle Compensator," filed Aug. 22, 2014, which, in turn claims priority under 35 U.S.C. §119 from U.S. provisional patent application Ser. No. 61/869,065, entitled "Broadband and Wide Field Angle Compensator," filed Aug. 23, 2013, the subject matter of which is incorporated herein by reference in its entirety.

TECHNICAL FIELD

The described embodiments relate to optical metrology systems, and more particularly to systems including rotatable compensator elements.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Optical metrology processes are used at various steps during a semiconductor manufacturing process to detect defects on wafers to promote higher yield. Optical metrology techniques offer the potential for high throughput without the risk of sample destruction. A number of optical metrology based techniques including ellipsometry, scatterometry, and reflectometry implementations and associated analysis algorithms are commonly used to characterize critical dimensions, film thicknesses, composition and other parameters of nanoscale structures.

As devices (e.g., logic and memory devices) move toward smaller nanometer-scale dimensions, characterization becomes more difficult. Devices incorporating complex three-dimensional geometry and materials with diverse physical properties contribute to characterization difficulty.

Optical ellipsometry has long been recognized as an effective, non-destructive measurement technique that provides accurate characterizations of semiconductor and other materials, surface conditions, layer composition and thickness, and overlying oxide layers. In particular, ellipsometry has proven useful to evaluate thickness, crystallinity, composition, and index of refraction characteristics of thin films deposited on semiconductor or metal substrates.

An ellipsometer probes a sample with a light beam having a known polarization state. The light beam is reflected at non-normal incidence from the surface of the sample. Upon reflection, the polarization state of the beam is modified depending upon the properties of the sample. By accurately measuring the polarization state of the reflected beam and comparing it to the original polarization state, various properties of the sample can be ascertained.

In spectroscopic ellipsometry, either the probing wavelength is changed and the ellipsometric measurement is repeated at each new wavelength, or the probe beam contains a multiplicity of wavelengths and the reflected beam is detected with spectral resolution. Spectroscopic ellipsometry is advantageous for characterization of multi-material samples formed in stacked layers. The different depth penetrations and spectral responses that depend on the material and wavelength of light provide additional information about a sample that is not available from single wavelength ellipsometers.

Many configurations have been proposed to measure the change in polarization state that occurs upon reflection. In one type of ellipsometer only two optical elements are used, a polarizer and an analyzer, one of which is held fixed and the other rotated. Such an ellipsometer, commonly called a rotating-polarizer or rotating-analyzer ellipsometer, is termed "an incomplete" polarimeter, because it is insensitive to the handedness of the circularly polarized component and exhibits poor performance when the light being analyzed is either nearly completely linearly polarized or possesses a depolarized component.

Limitations of rotating-polarizer and rotating-analyzer ellipsometers are reduced by including a rotating compensator placed between the polarizer and the analyzer. The compensator can be placed either between the sample and the polarizer, or between the sample and the analyzer. The compensator is an optical component that delays the light polarized parallel to its slow axis relative to light polarized parallel to its fast axis. The delay is proportional to the refractive index difference along the two directions and the thickness of the plate.

Compensators are most easily implemented in highly collimated beams of light. The highly collimated beam transmitted through the compensator acquires a uniform delay across its wavefront. This uniformity is generally desired for simplicity of analysis. Various compensator designs exist for use with highly collimated beams. By way of example, a compound zeroth order waveplate is used in the OP2xxx-OP9000 model family of Beam Profile Ellipsometers (BPE) manufactured by KLA-Tencor Corporation, Milpitas, Calif. (USA). The waveplate is an air-spaced, quartz bi-plate that is anti-reflection coated. A compound zeroth order waveplate is also used in the OP5xxx-OP7xxx model family of Spectroscopic Ellipsometers (SE) manufactured by KLA-Tencor Corporation, Milpitas, Calif. (USA). This waveplate is an air-spaced, magnesium fluoride ($MgF_2$) bi-plate. In another example, a $MgF_2$ monoplate is employed in the OP9000 family of spectroscopic ellipsometers manufactured by KLA-Tencor Corporation, Milpitas, Calif. (USA). All of these examples employ relatively thick (on the order of one millimeter) waveplates that are suitable for use with highly collimated light, but are not generally suitable for uncollimated light.

Other compensator designs include a Berek compensator, Fresnel rhomb, K-prism, and Soleil-Babinet compensator. All of these designs are sensitive to field angle and are only suitable for use within an ellipsometer employing highly collimated light.

In some examples, compensators are used in non-collimated beams of light. Different incident angles on the compensator have different directions of propagation inside the compensator, and thus generate different phase shifts and amplitudes. This results in a transmitted beam with a range of polarization states across the wavefront. This is described in greater detail in "Exact Theory of Retardation Plates by D. A. Holmes, J. Opt. Soc. Am, 54 (1964) 1115-1120, the entire content of which is incorporated herein by reference. To reduce the effect of varying incident angles, the thickness of the compensator elements may be reduced. For example, a thin (approximately ten micrometers), uniaxial quartz monoplate compensator is employed as part of a single wavelength elliposometer (SWE) incorporated into the Aleris product family manufactured by KLA-Tencor Corporation, Milpitas, Calif. (USA).

In general, thin, zeroth order waveplates are able to accommodate a larger field of view. But, these waveplates are typically thinner than the coherence length of the incident light. As a result, they suffer from phase and transmittance oscillations as a function of wavelength. This is a particular problem for ellipsometers operating with broadband light. Anti-reflection coatings reduce the amplitude of these oscillations, but typically only work well in a short wavelength range. Furthermore, broadband anti-reflection coatings can stress the waveplate, decreasing the retardation uniformity across the clear aperture. In general, free-standing, ultra-thin zeroth order waveplates cannot withstand the stress of even simple coatings. In the aforementioned monoplate compensator examples, the waveplate crystals (i.e., quartz and mica, respectively) are bonded to a thick (on the order of one millimeter) substrate of borosilicate (BK7) glass to provide mechanical stability and support for the crystals coated with anti-reflection coatings. Current manufacturing processes enable successful bonding of a very thin (approximately 10 micrometer) quartz crystal monoplate to the BK7 substrate. But, BK7 does not transmit ultraviolet light, and thus is unsuitable for use within a broadband ellipsometer including ultraviolet light.

Other compensator designs have been proposed for use with non-collimated light, including designs by Pancharatnam, Becker, Lyot, and designs incorporating biaxial polymers. These designs are described in greater detail in S. Pancharatnam, Proceedings of the Indian Academy of Sciences, A41, 130 (1955) and P. Yeh, C. Gu, "Optics of Liquid Crystal Displays," Chapters 4.7-4.10, Wiley (2010). The contents of each are incorporated herein by reference in their entireties.

The designs of Pancharatnam Becker, and Lyot use stacks of uniaxial or biaxial plates having two or more different materials. Each plate has a particular thickness and relative azimuthal orientation. Each of these designs includes regions of high dispersion when used with ultraviolet light. This makes them difficult to describe and stabilize. Furthermore, these compensators require usage in a fixed arrangement with respect to the polarizing element, making them inappropriate for use within a rotating element ellipsometer. This is also the case for the compensating plate described by J. D. de Veer in U.S. Pat. No. 3,904,267, issued Sep. 9, 1975, and incorporated herein by reference in its entirety.

Biaxial crystals require a specific relation between the principle refractive indices to provide a wide field of view. This can be engineered into polymers, but these polymers do not reliably transmit ultraviolet light. The inventors are not aware of any suitable biaxial crystals.

Existing compensator designs have failed to enable a rotating compensator ellipsometry tool operating with a non-collimated, broadband illumination source that includes ultraviolet wavelengths. Thus, an improved compensator design is desired.

SUMMARY

A rotatable, parallel plate compensator configured to transmit non-collimated light over a broad range of wavelengths, including ultraviolet, with a high degree of retardation uniformity across the aperture is presented.

In one embodiment, a rotatable compensator includes a stack of four individual plates in optical contact. Two plates in the middle of the stack are each made from a birefringent material that is cut with the optic axis in the plane of the entrance face and having a small thickness. These plates are arranged to form a low order, compound, zeroth order bi-plate. The remaining two plates are cut relatively thick and are made from an optically isotropic material. These plates are disposed on either end of the compound, zeroth order bi-plate. The low order, bi-plate minimizes the sensitivity of retardation across the aperture to non-collimated light. Materials are selected to ensure transmission of ultraviolet light. The optically isotropic end plates minimize coherence effects induced at the optical interface of the end plates and the surrounding environment.

In some embodiments, one or more additional plates of optically isotropic material are located between the birefringent plates. In some embodiments, a spatial separation is maintained between the birefringent plates or any other optically isotropic plates located between the birefringent plates.

In some other embodiments, an optically isotropic plate is located on only one side of the stack of birefringent plates.

In yet some other embodiments, a single birefringent plate is cut thin enough, that a zeroth order waveplate can be effectively realized from a single plate of birefringent material. In these embodiments, a relatively thick plate of isotropic material is located on one or both sides of the single, birefringent plate to minimize coherence effects.

The rotatable compensators described herein may be employed as part of systems configured to measure structural and material characteristics (e.g., material composition, dimensional characteristics of structures and films, etc.). Exemplary systems include ellipsometer or polarimeter systems incorporating a rotating compensator element. By way of example, rotating compensator ellipsometer (RCE) systems, dual rotating compensator (RCRC) systems, rotating polarizer, rotating compensator (RPRC) systems, and rotating compensator, rotating analyzer (RCRA) may incorporate rotatable compensator elements as described herein.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Rotatable compensators are presented which receive a non-collimated incident beam of light with a broad spectral range including ultraviolet wavelengths, and transform the polarization of the incident light such that the transmitted beam of light acquires a small range of delays across the wavefront. These rotatable compensators may be employed as part of systems configured to measure structural and material characteristics (e.g., material composition, dimensional characteristics of structures and films, etc.). Exemplary systems include ellipsometer or polarimeter systems incorporating a rotating compensator element. By way of example, rotating compensator ellipsometer (RCE) systems, dual rotating compensator (RCRC) systems, rotating polarizer, rotating compensator (RPRC) systems, and rotating compensator, and rotating analyzer (RCRA) may incorporate rotatable compensator elements as described herein.

Figure 1:
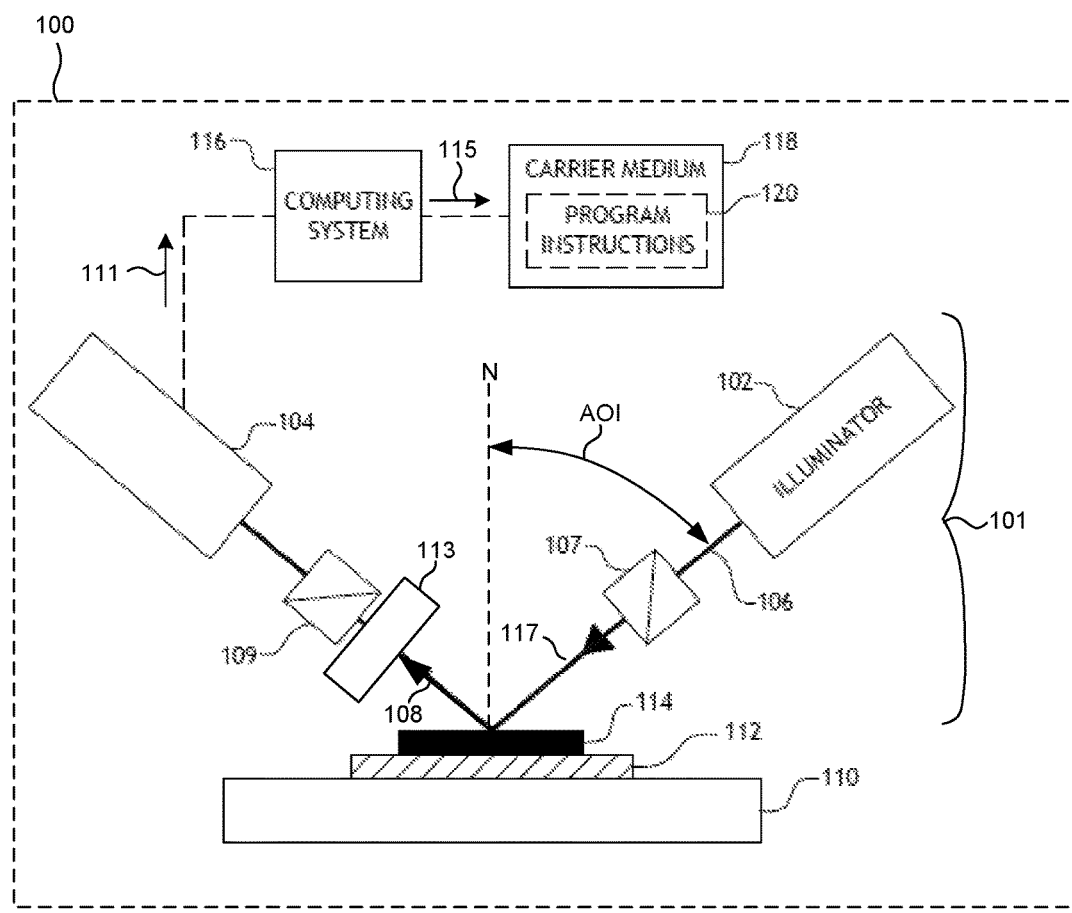
FIG. 1 is a diagram illustrative of a metrology system 100 including a rotatable, parallel plate compensator as described herein.

FIG. 1 illustrates a system 100 for measuring characteristics of a semiconductor wafer in accordance with the exemplary embodiments presented herein. System 100 may be used to perform spectroscopic ellipsometry measurements of one or more structures 114 of a semiconductor wafer 112 disposed on a wafer positioning system 110.

As depicted in FIG. 1, system 100 includes a rotating compensator ellipsometer (RCE) 101. In one aspect, RCE 101 includes a rotatable compensator 113 configured in any of the non-limiting, exemplary embodiments described herein. RCE 101 simultaneously (or nearly simultaneously) measures the polarization states of a broad range of wavelengths contained in a probe beam 108 reflected from a test sample 114. RCE 101 includes a broadband illumination source 102, a polarizer 107, a rotatable compensator 113, an analyzer 109, and a detector 104.

Illumination source 102, by way of non-limiting example, includes one or more light sources that produce a spectrum of polychromatic light over a predetermined wavelength range of interest including wavelengths in the ultraviolet spectrum. In some examples, illumination source 102 generates illumination light in a range between 190 nanometers and 880 nanometers. Illumination source 102 may include one or more laser-based light sources, arc-lamp sources, gas-filled bulb sources, etc. In general, any light source configured to emit short coherence length light, and in particular, UV light down to 190 nanometers may be contemplated. It is contemplated that in addition to generating light having one or more wavelengths in the range between 190 and 880 nanometers, illumination source 102 may be configured to generate light including wavelengths below 190 nanometers, above 880 nanometers, or both.

The diverging beam 106 from illumination source 102 interacts with polarizer 107 to create a known polarization state. The polarizer 107 may be, for example, a quartz Rochon prism. In general, the polarization does not necessarily have to be linear, or even complete. Polarizer 107 may be made of any of a variety of materials. Polarizer 107 could include reflection polarizers suitable for ultraviolet wavelengths. These polarizers may be contained within a vacuum environment. The azimuth angle of polarizer 107 is oriented so that the plane of the electric vector associated with the linearly polarized beam 117 exiting from the polarizer 107 is at a known angle with respect to the plane of incidence (defined by the propagation direction of the beam 117 and the normal, N, to the exposed surface of the sample 114). The polarizer 107 can be omitted if a particular light source is used that emits light with the desired known polarization state.

Beam 117 is incident on, and reflects from, sample 114 at an oblique angle. As depicted in FIG. 1, sample 114 is a thin layer formed on a wafer substrate 110. However, in general, the sample 114 can be bare, or multiple layers can exist one on top of the other. Based upon well known ellipsometric principles, the reflected beam 108 will generally be in a different elliptically polarized state after interacting with the sample 114, as compared to the polarization state of the incoming beam 117.

Beam 108 reflected from the sample 114 passes through a rotatable compensator 113, which introduces a relative phase delay (i.e., phase retardation), $\Delta$, between light polarized parallel to its slow axis relative to light polarized parallel to its fast axis. The amount of phase retardation is a function of the wavelength, the dispersion characteristics of the material used to form the compensator 113, and the thickness of the compensator 113. Compensator 113 is rotated to a multiplicity of angles, about an axis substantially parallel to the propagation direction of beam 108. By way of non-limiting example, compensator 113 is rotated by an electric motor (not shown).

Compensator 113 is configured such that a desired range of phase delay of the beam 108 is induced by the range of wavelengths used to probe the sample 114. The rotatable compensator 113 changes the polarization state of the beam 108 as it rotates in a known way. Beam 108 then interacts with analyzer 109, which extracts a substantially single, known polarization state. Analyzer 109 may be, for example, a linear polarizer oriented at an azimuth angle of 45 degrees relative to the plane of incidence. However, in general, any optical device that serves to appropriately extract a substantially single, known polarization state can be used as an analyzer.

It should be noted that compensator 113 is located between sample 114 and analyzer 109 (as shown in FIG. 1) in some embodiments. However, in some other embodiments, compensator 113 is located between sample 114 and polarizer 107. In some other embodiments, a compensator such as compensator 113 is located between sample 114 and analyzer 109, and also between sample 114 and polarizer 107.

As depicted in FIG. 1, beam 108 enters detector 104 after passing through rotatable compensator 113 and analyzer 109. Detector 104 measures the intensity of different wavelengths of light throughout the wavelength range of interest. By measuring the intensity of the light transmitted by analyzer 109, the polarization state of beam 108 reflected from the sample can be determined.

Detector 104 may include a dispersive element (not shown), such as a diffraction grating, prism, or holographic plate, to angularly disperse the beam 108 as a function of wavelength to individual detector elements contained in a detector array within the detector 104. In some embodiments, the detector 104 may include a CCD camera, or a photomultiplier with suitably dispersive or otherwise wavelength selective optics. In some other embodiments, the detector may be include a monochromator, etc., and the different wavelengths may be measured serially (one wavelength at a time) using a single detector element.

As depicted in FIG. 1, output signals 111 indicative of the intensity information measured by the detector 104 is received by computing system 116. Computing system 116 determines the properties of the sample by comparing the detector signal to a model of that signal based on the calibrated optical properties of the system components and a model of the optical properties of the sample. Typically, this includes measuring the beam intensity as a function of wavelength, and also measuring beam intensity as a function of the azimuth (rotational) angle of the compensator about its axis of rotation (which is substantially parallel to the propagation direction of beam 108). This measurement of intensity as a function of compensator rotational angle may be a measurement of the intensity of beam 117 as a function of time, when the compensator angular velocity is known.

In some embodiments, the compensator 113 is rotated incrementally, stopped at each incremental angle, and data is collected while the compensator is stationary. However, in some other preferred embodiments, the compensator is rotated substantially continuously, and data is collected while the compensator is moving. In these embodiments, the collected data is typically corrected for the averaging that occurs as a result of the movement of the compensator during a data-acquisition interval.

In a preferred embodiment, ellipsometer 101 is configured as a rotating polarizer, rotating compensator ellipsometer (RPRCE). The compensator 113 is installed on a motor shaft between the collection mirrors (not shown) and analyzer 109. Compensator 113 rotates at some harmonic or subharmonic frequency of the rotating polarizer. The data collection is synchronized with the rotations of both the polarizer and compensator.

It should be recognized that the various computational steps described throughout the present disclosure may be carried out by a single computer system 116, or alternatively, a multiple computer system 116. Moreover, different subsystems of the system 100, such as the detector 104, may include a computer system suitable for carrying out at least a portion of the steps described herein. Therefore, the aforementioned description should not be interpreted as a limitation on the present invention but merely an illustration.

In addition, the computer system 116 may be communicatively coupled to any of the detector 104, illuminator subsystem 102, rotatable compensator 113, analyzer 109, or polarizer 107 of the ellipsometer 101 in any manner known in the art. The computer system 116 of the system 100 may be configured to receive and/or acquire data or information from the subsystems of the system (e.g., spectrometer 104, illuminator 102, and the like) by a transmission medium that may include wireline and/or wireless portions. In this manner, the transmission medium may serve as a data link between the computer system 116 and other subsystems of the system 100.

In one example, computing system 116 receives the measured data from each detector, and is programmed with software for processing the data it receives in an appropriate manner. The spectral response 115 of a specimen may be inferred from the measured data by analyzing the changes in polarization of radiation reflected from the sample in response to incident radiation having known polarization state in any number of ways known in the art. Furthermore, the measured spectral response 115 may be stored in a memory (e.g., carrier medium 118).

Any of compensator 113, polarization state generator 107 and polarization state analyzer 109 may be configured to rotate about their optical axis during a measurement operation. In some examples, computing system 116 is programmed to generate control signals to control the azimuthal orientation of any of compensator 113, polarization state generator 107, polarization state analyzer 109, or other elements of the system 100 (e.g., wafer positioning system 110 upon which specimen 112 rests). Computing system 116 may also receive data indicative of the azimuthal orientation of any of compensator 113, polarization state analyzer 109, and polarization state generator 107 from a position sensor associated with any of these elements. Computing system 116 may be programmed with software for processing such orientation data in an appropriate manner.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a magnetic or optical disk, or a magnetic tape.

Moreover, a rotating compensator system that requires highly collimated illumination (e.g., less than one milliradian divergence) may be more costly, both in terms of the type of source used, the amount of light wasted, and the space required to realize the highly collimated beam.

In one aspect, a rotatable compensator that transmits light having a temporal coherence length that is long relative to the thickness of the birefringent material of the compensator, over a range of field angles (e.g., at least five milliradians), and over a broad range of wavelengths including ultraviolet wavelengths (e.g., transmissive over the entire range of wavelengths between 190-880 nanometers) is described herein. In some examples, the rotatable compensator is at least 90% transmissive for light having any wavelength within a range between 190 and 880 nanometers. In some examples, the rotatable compensator is at least 50% transmissive for light having any wavelength within a range between 190 and 880 nanometers. In yet some other examples, the rotatable compensator is at least 10% transmissive for light having any wavelength within a range between 190 and 880 nanometers.

Figure 2:
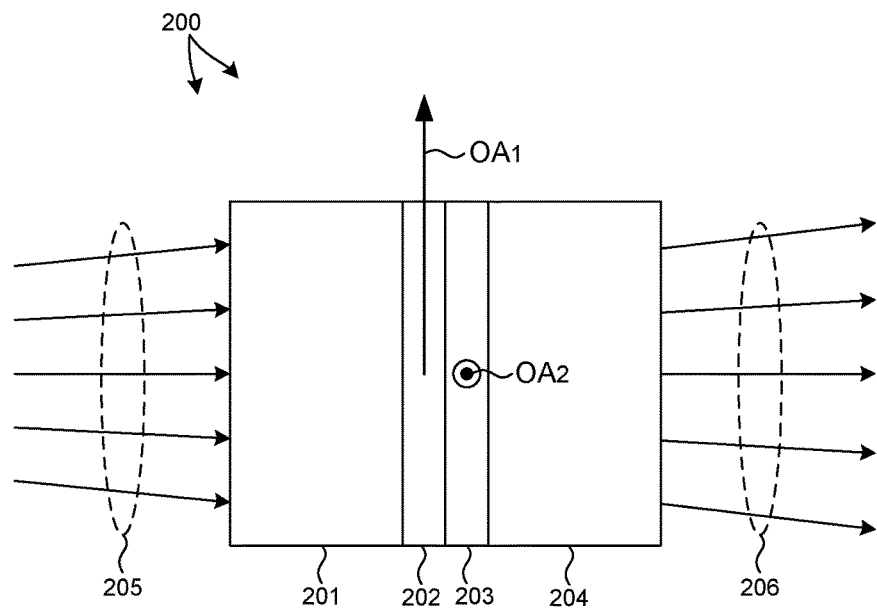
FIG. 2 is a diagram illustrative of a rotatable, parallel plate compensator 200 in one embodiment.

FIG. 2 illustrates a rotatable compensator 200 in one preferred embodiment. Compensator 200 includes a stack of four individual plates, each in optical contact with any adjacent plate in the stack. Plates 202 and 203 are made from a birefringent material (e.g., quartz, magnesium fluoride, sapphire, beta barium borate, lithium tetraborate, cesium lithium borate, potassium dihydrogen phosphate, ammonium dihydrogen phosphate, etc.). Plates 202 and 203 are each low order and are arranged to form a compound zeroth order, bi-plate. Plates 201 and 204 are made from an optically isotropic material (e.g., fused silica, fused quartz (or quartz glass), calcium fluoride, lithium fluoride, barium fluoride, diamond, etc). Plates 201 and 204 are disposed on either side of the bi-plate formed by plates 202 and 203.

Compensator 200 may be used in the same manner as any parallel plate compensator. Light 205 of some polarization state enters the compensator 200 at nominally normal incidence and light 206 exits the compensator 200 in a different, but deterministic, polarization state. In one example, the divergence of light 205 entering compensator 200 can be as large as ten milliradians, while light 206 exiting compensator 200 has less than 0.1 degrees of induced phase variation over the beam due to the beam divergence up to approximately ten milliradians. In some examples, the divergence of light 205 entering compensator 200 can be even larger than ten milliradians, while light 206 exiting compensator 200 has less than 0.1 degrees of induced phase variation over the beam.

Figure 7:
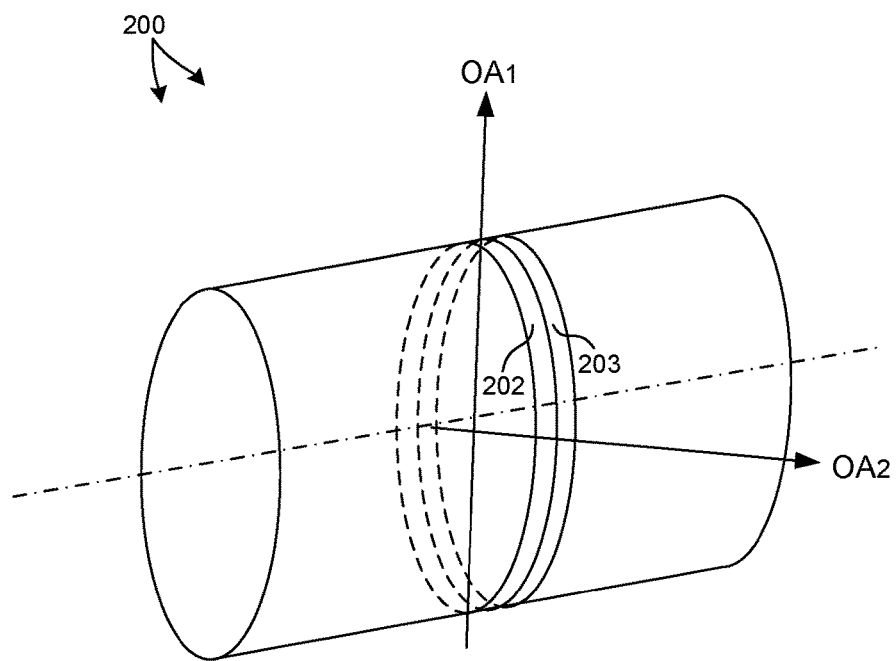
FIG. 7 is a diagram illustrative of a perspective view of the rotatable, parallel plate compensator 200 illustrated in FIG. 2.

In one example, plates 201 and 204 are made from fused silica and plates 202 and 203 are made from single crystal quartz. Plate 202 includes a layer of quartz cut with the optic axis, OA1, (i.e., c-axis or extraordinary axis) oriented parallel to the parallel, planar faces of plate 202 within a tolerance of approximately 0.1 degrees. In general, the thinner the birefringent plate or plates, the larger the field of view for a given retardation uniformity. In practice, it may not be possible to manufacture a single, birefringent plate that is thin enough to provide single plate, zeroth order operation over a desired range of wavelengths. In these examples, a compound, zeroth order bi-plate may be made from thin, low-order plates that can be manufactured. In one embodiment, plate 202 is a single crystal quartz plate cut to a thickness of 40 micrometers. A thickness of 40 micrometers implies that, by itself, plate 202 cannot function as a true, zero order waveplate over a wavelength range from 190-880 nanometers. Hence, plate 203 is arranged to form a compound zeroth order, bi-plate, in combination with plate 202. Plate 203 includes a layer of quartz also cut with the optic axis, OA2, (i.e., c-axis or extraordinary axis) oriented parallel to the parallel, planar faces of plate 203 within a tolerance of approximately 0.1 degrees. As depicted in FIG. 2, the optic axis, OA2, extends outward from the drawing page. In one embodiment, plate 203 is cut to a thickness of 51 micrometers to achieve the desired retardation spectrum. In general, the thicknesses of plates 202 and 203 are selected to be as thin as possible with a thickness difference chosen to provide a compound zeroth order waveplate with a desired retardation spectrum. In some examples, plates 202 and 203 are cut to a thickness less than five hundred micrometers to minimize induced phase variation over the beam due to the beam divergence to a desired level. In some examples, plates 202 and 203 are cut to a thickness less than one hundred micrometers to minimize induced phase variation over the beam due to the beam divergence to a desired level. In general, the difference in thickness of plates 202 and 203 is selected to provide a compound zeroth order waveplate with a desired retardation spectrum. In some examples, the difference in thickness of plates 202 and 203 is less than one hundred micrometers. In some examples, the difference in thickness of plates 202 and 203 is less than twenty micrometers. In the embodiment depicted in FIG. 2, plates 202 and 203 are optically contacted at the free quartz surfaces to form a waveplate. Plates 202 and 203 are oriented with respect to one another such that the azimuth angle between their respective optic axes is ninety degrees within an alignment tolerance. FIG. 7 illustrates an isometric view of compensator 200 highlighting the optic axis, OA1, associated with plate 202 and the optic axis, OA2, associated with plate 203. As depicted in FIG. 7, the azimuth angle formed between OA2 and OA1 is approximately ninety degrees. Any variation from a nominally perpendicular alignment of the optic axes associated with plates 202 and 203 causes the optical behavior of the waveplate formed from plates 202 and 203 to deviate from linear (linearly polarized eigenstates) by introducing slightly elliptical behavior (elliptically polarized eigenstates). However, in practice, it has been found that in some examples, an alignment tolerance of two degrees is acceptable. In some other examples, an alignment tolerance of five degrees is acceptable.

In one further aspect, birefringent plates 202 and 203 are optically contacted to isotropic plates 201 and 204, respectively. The refractive index of the isotropic plates is chosen to match as nearly as possible the mean refractive index of the birefringent material comprising the compensator plate or plates. The index matching frustrates reflection at the surfaces of the birefringent material over a wide spectral range. In some examples, isotropic plates 201 and 204 are made from fused silica to closely match the index of refraction of crystalline quartz; thus minimizing reflections at each interface. In this example, the refractive index of the optically isotropic plate is within 6% of a mean refractive index of the birefringent plate. In addition, fused silica is selected for its transmission properties in the ultraviolet spectrum. In some examples, the refractive index of the optically isotropic plate is within 15% of a mean refractive index of the birefringent plate. In some examples, the refractive index of the optically isotropic plate is within 25% of a mean refractive index of the birefringent plate.

However, reflections still occur at the glass-air interfaces. The thickness of the optically isotropic plates is chosen to be significantly longer than the coherence length of the light transmitted through the system in which the compensator is used. This minimizes coherence effects. In some examples, the thickness of plates 201 and 204 is greater than 0.5 millimeters. The thickness of plates 201 and 204 need not be precise nor equal. In one example, the thickness of the plates 201 and 204 is approximately one millimeter.

Figure 3:
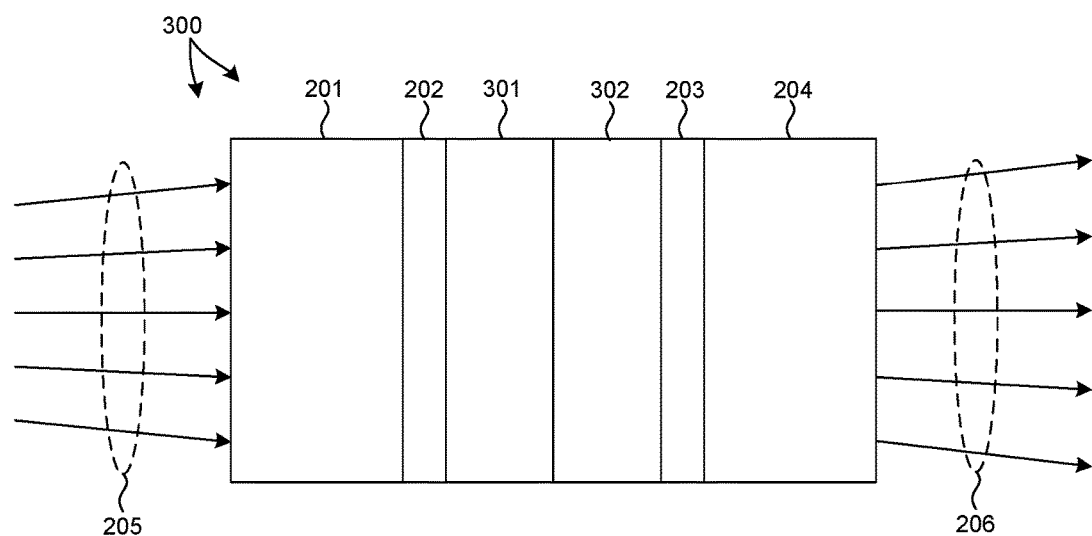
FIG. 3 is a diagram illustrative of a rotatable, parallel plate compensator 300 in another embodiment.

FIG. 3 illustrates a rotatable compensator 300 in another embodiment. Like numbered elements are similar to those described with reference to FIG. 2. Compensator 300 includes the stack of individual plates 201-204 described with reference to FIG. 2, however, in addition, one or more optically isotropic plates (e.g., optically isotropic plates 301 and 302) are disposed between birefringent plates 202 and 203, such that optical contact is made among plates 202, 203, and any intervening optically isotropic plates.

This design has been found to provide similar optical performance as described with reference to compensator 200. Although, more complex compared to compensator 200, compensator 300 may offer some advantage with respect to manufacture. For example, birefringent plate 202 may be sandwiched between optically isotropic plates 201 and 301 with a minimum of induced mechanical strain. Similarly, birefringent plate 203 may be sandwiched between optically isotropic plates 302 and 204 with a minimum of induced mechanical strain. In a final assembly step, these two subassemblies may be brought in to optical contact at the interface between plates 301 and 302 with precise alignment, and without inducing significant mechanical strain on the birefringent plates 202 and 203.

Figure 4:
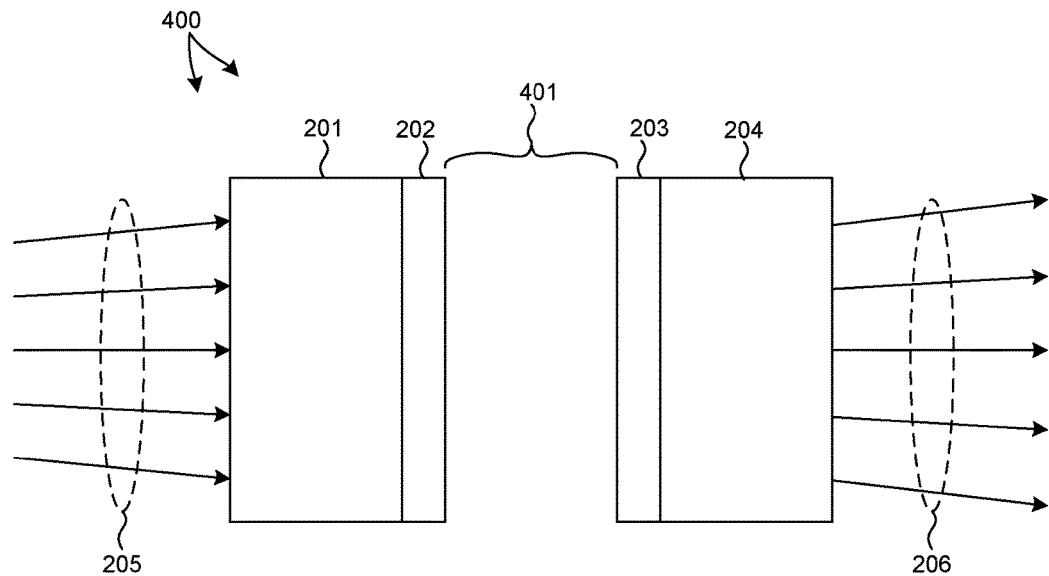
FIG. 4 is a diagram illustrative of a rotatable, parallel plate compensator 400 in yet another embodiment.

FIG. 4 illustrates a rotatable compensator 400 in yet another embodiment. Like numbered elements are similar to those described with reference to FIG. 2. Compensator 400 includes the stack of individual plates 201-204 described with reference to FIG. 2, however, a spatial gap 401 is maintained between birefringent plates 202 and 203. Gap 401 may be void (e.g., held in vacuum) or filled with any suitable gas or mixture of gases (e.g., air, nitrogen, argon, etc.). In another embodiment (not shown), a gap may be introduced between optically isotropic plates 301 and 302 of compensator 300 depicted in FIG. 3. In this manner, birefringent plates 202 and 203 are separated by a combination of one or more optically isotropic plates and a spatial gap that is void or filled with any suitable gas or gas mixture.

The introduction of gap 400 between birefringent plates 202 and 203 provides both advantages and disadvantages compared to compensator 200. The primary disadvantage is the introduction of additional phase and amplitude oscillations into the transmitted light beam as a function of wavelength. These oscillations arise from the large reflectivity at the interface between 202 and 401 and at the interface between 203 and 401. These oscillations are present even when the separation of the birefringent plates is much larger (e.g., 100×) than the coherence length of the transmitted light. However, the primary advantage is that the rotational alignment of the optic axes (e.g., OA1 and OA2) of the two birefringent plates 202 and 203 may be performed much more precisely when a gap is maintained between the plates. For example, the optic axes of plates 202 and 203 may be aligned at ninety degrees with a tolerance of less than 15 arc seconds when a gap is maintained between the two plates. In this manner, the waveplate is more linear. In some examples, this advantage may outweigh the disadvantages of the induced spectral fringes. For example, if compensator 400 is used at a few discrete wavelengths, the retardation at each wavelength may be determined independently. With this relationship established apriori, the induced spectral fringes would not be detrimental.

Figure 5:
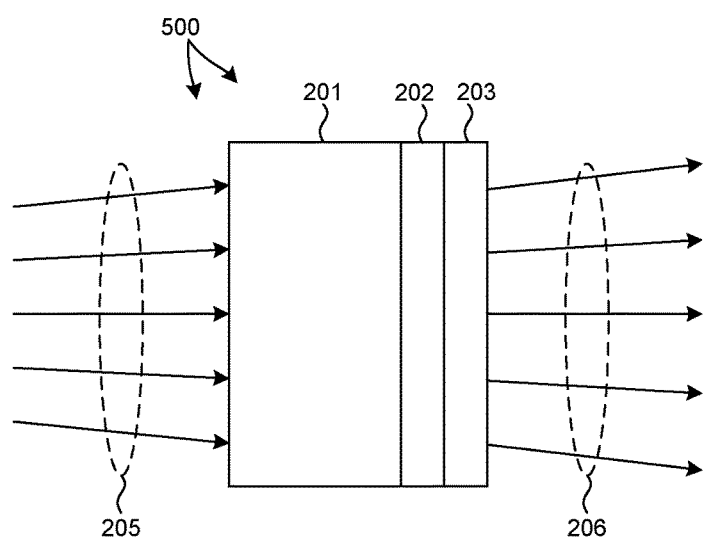
FIG. 5 is a diagram illustrative of a rotatable, parallel plate compensator 500 in yet another embodiment.

FIG. 5 illustrates a rotatable compensator 500 in another embodiment. Like numbered elements are similar to those described with reference to FIG. 2. Compensator 500 is similar to the stack of individual plates 201-204 described with reference to FIG. 2, except that one of the optically isotropic plates (e.g., plate 204) is not included in the assembly. The performance of this design may be acceptable in many applications, but it has been found that providing an optically isotropic plate at both ends of the compensator stack (e.g., as depicted in the embodiments illustrated in FIGS. 2-4 and FIG. 6) provides an improved optical performance compared to a design that includes an optically isotropic plate at only one end of the compensator stack. More specifically, the induced coherence oscillation amplitude of retardation, particularly at longer wavelengths, is significantly reduced when optically isotropic plates are included on both ends of the compensator stack.

Figure 6:
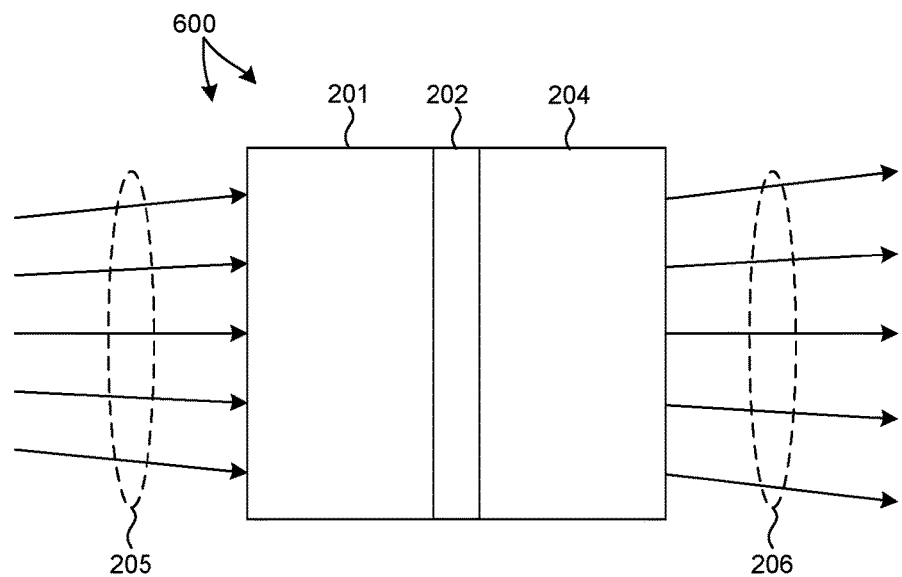
FIG. 6 is a diagram illustrative of a rotatable, parallel plate compensator 600 in yet another embodiment.

FIG. 6 illustrates a rotatable compensator 600 in another embodiment. Like numbered elements are similar to those described with reference to FIG. 2. Compensator 600 is similar to the stack of individual plates 201-204 described with reference to FIG. 2, except that one of the birefringent plates (e.g., plate 203) is not included in the assembly. In general, it is not essential that the compensator be a bi-plate. A single birefringent plate may be stacked between two optically isotropic plates to achieve an acceptable optical performance. In some examples, the compensator may be utilized as a multi-order waveplate. The single plate compensator 600 has all the advantages previously listed. In addition, it does not require the alignment of two birefringent plates. For beams having up to 10 milliradians of divergence over a range of wavelengths between 190 and 880 nanometer, a quartz waveplate should be less than 100 micrometers thick to keep distortion of the retardation across field angle below 0.1 degree. In some examples, a quartz waveplate having a thickness less than 50 micrometers is employed.

In yet another embodiment, a compensator is contemplated that is similar to compensator 600 except that one of the optically isotropic plates (e.g., plate 204) is not included in the assembly. As discussed with reference to compensator 500 of FIG. 5, the performance of this design may be acceptable in many applications, but it has been found that providing an optically isotropic plate at both ends of the compensator stack (e.g., as depicted in the embodiments illustrated in FIGS. 2-4 and FIG. 6) provides an improved optical performance compared to a design that includes an optically isotropic plate at only one end of the compensator stack.

In general, more than two birefringent plates constructed of the same, or different materials, may be employed. This may be desirable to implement temperature compensated and achromatic designs. The addition of optically isotropic plates at each end of the compensator reduces coherence effects for these designs.

Although the embodiments discussed herein are explained with reference to system 100, any optical metrology system configured to illuminate and detect light reflected, transmitted, or diffracted from a specimen and take advantage of a rotatable compensator may be contemplated. Exemplary systems include an angle-resolved ellipsometer or polarimeter, a scatterometer, an ellipsometer or polarimeter, a spectroscopic ellipsometer or polarimeter, a multi-wavelength, two-dimensional beam profile ellipsometer or polarimeter, a rotating compensator spectroscopic ellipsometer or polarimeter, etc. By way of non-limiting example, an ellipsometer may include a single rotating compensator, multiple rotating compensators, a rotating polarizer, a rotating analyzer, a modulating element, multiple modulating elements, or no modulating element.

A system implementing the compensators described herein may also be configured in a number of different ways. For example, a wide range of wavelengths (including visible, ultraviolet, and infrared), angles of incidence, states of polarization, and states of coherence may be contemplated. In another example, the system may include any of a number of different light sources (e.g., a directly coupled light source, a laser-sustained plasma light source, etc.). In another example, the system may include elements to condition light directed to or collected from the specimen (e.g., apodizers, filters, etc.).

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "rotatable compensator" or "rotatable compensator element" refers to a compensator suitable for use in a rotating compensator measurement system, including measurement systems employing continuously rotating compensators or non-continuously rotating compensators.

As described herein, the term "critical dimension application" or "critical dimension measurement application" includes any critical dimension measurement.

As described herein, the term "metrology system" includes any system employed at least in part to characterize a specimen in any aspect. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, back-side inspection tool, macro-inspection tool, or multi-mode inspection tool (involving data from one or more platforms simultaneously), and any other metrology or inspection tool that benefits an ellipsometer, polarimeter or scatterometer with a rotating compensator.

Various embodiments are described herein for a semiconductor processing system (e.g., an inspection system or a lithography system) that may be used for processing a specimen. The term "specimen" is used herein to refer to a site on a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A parallel plate compensator, comprising:
    a first birefringent plate having a front surface, back surface, an optic axis oriented in a plane parallel to the front and back surfaces within a manufacturing tolerance, and a thickness of less than five hundred micrometers;
    a second birefringent plate having a front surface, a back surface, an optic axis oriented in a plane parallel to the front and back surfaces within the manufacturing tolerance, and a thickness of less than five hundred micrometers; and
    a first optically isotropic plate in optical contact with the front surface of the first birefringent plate, the optically isotropic plate having a thickness of at least five hundred micrometers, wherein a refractive index of the optically isotropic plate is within 15% of a mean refractive index of the first birefringent plate.

2. The parallel plate compensator of claim 1, further comprising:
    a third birefringent plate having a front surface, a back surface, an optic axis oriented in a plane parallel to the front and back surfaces within the manufacturing tolerance, and a thickness of less than five hundred micrometers.

3. The parallel plate compensator of claim 1, wherein a material composition of the first birefringent plate and a material composition of the second birefringent plate are the same.

4. The parallel plate compensator of claim 1, wherein the thickness of the first birefringent plate is the same thickness as the thickness of the second birefringent plate.

5. The parallel plate compensator of claim 1, wherein a back surface of the first birefringent plate and a front surface of the second birefringent plate are in optical contact.

6. The parallel plate compensator of claim 1, wherein a difference in the thickness of the first birefringent plate and the thickness of the second birefringent plate is less than 100 micrometers.

7. The parallel plate compensator of claim 1, wherein the first and second birefringent plates are made from any of a single crystal quartz material, a magnesium fluoride material, a beta barium borate material, a lithium tetraborate material, a cesium lithium borate material, a potassium dihydrogen phosphate material, and an ammonium dihydrogen phosphate material.

8. The parallel plate compensator of claim 1, wherein the optic axis of the first birefringent plate is aligned at ninety degrees with the optic axis of the second birefringent plate with a tolerance of five degrees.

9. The parallel plate compensator of claim 1, wherein the first optically isotropic plate is made from any of a fused silica material, a fused quartz material, a calcium fluoride material, a lithium fluoride material, a barium fluoride material, and a diamond.

10. The parallel plate compensator of claim 1, wherein the field of view is at least 5 milliradians.

11. The parallel plate compensator of claim 1, wherein the parallel plate compensator is at least 10% transmissive for light having any wavelength within a range between 190 and 880 nanometers.

12. A parallel plate compensator, comprising:
   two or more birefringent plates each having a front surface, a back surface, an optic axis oriented in a plane parallel to the front and back surfaces within a manufacturing tolerance, and a thickness of less than 500 micrometers; and
   a first optically isotropic plate in optical contact with a front surface of a first birefringent plate of the two or more birefringent plates, the first optically isotropic plate having a thickness of at least five hundred micrometers, wherein a refractive index of the first optically isotropic plate is within 15% of a mean refractive index of the first birefringent plate, and wherein the parallel plate compensator is at least 10% transmissive for light having any wavelength within a range between 190 and 880 nanometers.

13. The parallel plate compensator of claim 12, further comprising:
   a second optically isotropic plate in optical contact with a front or back surface of a second birefringent plate of the two or more birefringent plates, the back surface of the first birefringent plate, or both, the second optically isotropic plate having a thickness of at least five hundred micrometers, wherein a refractive index of the second optically isotropic plate is within 15% of a mean refractive index of at least one of the two or more birefringent plates.

14. An ellipsometer, comprising:
   an illumination source configured to generate non-collimated, polychromatic illumination light directed toward a sample;
   a parallel plate compensator configured to transmit an amount of the illumination light, wherein the parallel plate compensator comprises,
   a first birefringent plate having a front surface, a back surface, an optic axis oriented in a plane parallel to the front and back surfaces within a manufacturing tolerance, and a thickness of less than five hundred micrometers;
   a second birefringent plate having a front surface, a back surface, an optic axis oriented in a plane parallel to the front and back surfaces within the manufacturing tolerance, and a thickness of less than five hundred micrometers; and
   a first optically isotropic plate in optical contact with the front surface of the first birefringent plate,
   an analyzer configured to extract a polarization state from the amount of light transmitted through the parallel plate compensator; and
   a detector configured to measure an intensity of an amount of light transmitted through the analyzer at different wavelengths throughout a wavelength range of interest that includes ultraviolet wavelengths.

15. The ellipsometer of claim 14, wherein the compensator is disposed in an optical path between the specimen and the analyzer.

16. The ellipsometer of claim 14, wherein the compensator is disposed in an optical path between the specimen and the polarizer.

17. The ellipsometer of claim 14, wherein the parallel plate compensator is rotatable about an axis that is perpendicular to a face of the parallel plate compensator.

18. The ellipsometer of claim 14, the parallel plate compensator further comprising:
   a third birefringent plate having a front surface, a back surface, an optic axis oriented in a plane parallel to the front and back surfaces within the manufacturing tolerance, and a thickness of less than five hundred micrometers.

19. The ellipsometer of claim 14, wherein the back surface of the first birefringent plate and the front surface of the second birefringent plate are in optical contact.

20. The ellipsometer of claim 14, wherein the parallel plate compensator is at least 10% transmissive for light having any wavelength within a range between 190 and 880 nanometers.

* * * * *